US005877732A

United States Patent [19]
Ziarati

[11] Patent Number: 5,877,732
[45] Date of Patent: Mar. 2, 1999

[54] THREE-DIMENSIONAL HIGH RESOLUTION MRI VIDEO AND AUDIO SYSTEM AND METHOD

[75] Inventor: Mokhtar Ziarati, No. Hollywood, Calif.

[73] Assignee: Resonance Technology Co., Northridge, Calif.

[21] Appl. No.: 644,841

[22] Filed: May 8, 1996

Related U.S. Application Data

[63] Continuation of Ser. No. 226,995, Apr. 13, 1994.
[51] Int. Cl.⁶ .................................................. G09G 5/00
[52] U.S. Cl. .............................. 345/8; 128/653.2; 348/77
[58] Field of Search .................................. 345/7, 8, 9, 87, 345/32; 324/318; 128/653.1, 653.2; 348/46, 47, 48, 51, 52, 53, 77, 61

[56] References Cited

U.S. PATENT DOCUMENTS

| 4,613,820 | 9/1986 | Edelstein et al. | 324/318 |
| 4,733,189 | 3/1988 | Punchard | 324/318 |
| 4,864,192 | 9/1989 | Buckwald et al. | 315/8 |
| 4,901,141 | 2/1990 | Costello | 324/318 |
| 5,076,275 | 12/1991 | Belmor | 324/318 |
| 5,101,139 | 3/1992 | Lechter | 315/85 |
| 5,134,373 | 7/1992 | Tsuruno | 324/318 |
| 5,184,074 | 2/1993 | Kaufman et al. | 324/318 |
| 5,334,991 | 8/1994 | Wells et al. | 345/8 |
| 5,339,813 | 8/1994 | De Yoe | 128/653.1 |
| 5,412,419 | 5/1995 | Ziarati | 348/61 |
| 5,432,544 | 7/1995 | Ziarati | 348/61 |

FOREIGN PATENT DOCUMENTS

3844482 C1  12/1988  Germany .

OTHER PUBLICATIONS

*Sony Samples Tiny LCDs* by A.R. Thryft, EBN optical magazine, Products section, Product of the Week, Sep. 13, 1993, p. 31.

Edmund Scientific Borescope by Edmund Scientific Company, 101 E.
Gloucester Pike, Barrington, NJ 08007–1380, 1993 Annual Reference, Catalog for Optics, Science and Education, vol. 13N1, p. 79.
Advance for Radiologic Science Professionals—Cat Scanning vol. 4, No. 2, Jan. 14, 1991, p.10—"Television comes to MRI Scanner".

(List continued on next page.)

*Primary Examiner*—Dennis-Doon Chow
*Attorney, Agent, or Firm*—Larry K. Roberts

[57]  ABSTRACT

A three-dimensional high resolution magnetic resonance imaging (MRI) video and audio system employed within the magnetic field of a bore of an MRI scanner to provide video images via a relay lens system and corresponding audible sound via a non-magnetic path to an MRI patient. The invention provides non-magnetic video sources and audio speakers for generating the images and sound, respectively, and includes a first non-magnetic shielded generating mechanism positioned within the magnetic field of the bore for providing a video image. A first optical mechanism captures and transmits the generated video image to provide a high resolution video image. A second optical mechanism magnifies and redirects the high resolution video image for viewing by the patient. A second non-magnetic shielded generating mechanism is positioned within the magnetic field of the bore for providing audible sound over the full frequency range. In a preferred embodiment, twin optical systems each receive a video signal supplied by a video source to a liquid crystal display (LCD) panel for providing a video image. The video image is impressed upon and travels across a relay lens system to a multi-element eyepiece prism and lens assembly. Each eyepiece assembly utilizes a combination of lenses to magnify the image and a prism to refract the image into the eye of the viewer in the scanner tunnel. Likewise, twin audio systems each receive audio signals supplied by an audio source to a non-magnetic shielded transducer. The audio signals are converted to audible sound over the full frequency range and transmitted to a noise canceling headset via a short non-magnetic path.

39 Claims, 6 Drawing Sheets

OTHER PUBLICATIONS

Magnetic Resonance in Medicine 210–221—Patient Anesthesia and Monitoring at a 1.5–T MRI Installation—Received Dec. 7, 1987; revised Jan. 21, 1988—S.J. Karlik, et al.

Site Planning Design: Influences and Implementation—Einstein and Hilal, Magnetic Resonance Annual 1985, S267–311, MT540:Z121.

Practical NMR Imaging—MA Foster & JMS Hutchison—1987.

A Handbook Series on Electromagnetic Interference and Compatibility (EMI Control Methods and Techniques) by Donald RJ White, MSEE/PE—Copyright 1973 Third Edition 1981.

A handbook on Shielding Design Methodology and Procedures by Donald RJ White, MSEE/PE—Interference Control Technologies—copyright 1986.

A Handbook Series on Electromagnetic Interference and Compatibility—vol. 4—Filters and Power Conditioning—Interference Control Technologies, Inc.—1988.

A Handbook Series on Electromagnetic Interference and Compatibility—vol. 3—Electromagnetic Shielding—Donald RJ White and Michel Mardiguian—1988 by emf–emi control, Inc.

R. Rokey et al., "Monitoring of Acutely Ill Patients during Nuclear Magnetic Resonance Imaging: Use of a Time–Varying Filter electrocardiographic Gating Device to Reduce Gradient Artifacts," *Magnetic Resonance in Medicine 6, 240–245 (1988)*.

THREE-DIMENSIONAL HIGH RESOLUTION MRI VIDEO AND AUDIO SYSTEM AND METHOD

"This application is a continuation of copending application Ser. No. 08/226,995 filed on Apr. 13, 1994".

BACKGROUND OF THE INVENTION

1. Field of the Invention

The present invention relates to video and audio systems. More specifically, the present invention relates to methods and apparatus for a combined video and audio system that provides three-dimensional, high resolution video images and corresponding audible sound over the full frequency range to a patient positioned in an MRI electromagnetic environment.

2. Description of the Related Art

A magnetic resonance imaging (MRI) scanner is a medical diagnostic apparatus employed to generate images of soft tissue of the human body which are not otherwise visible, for example, by the use of x-rays. In general, the MRI scanner includes a tunnel area which accommodates a patient lying, for example, in the supine position. The tunnel area is surrounded by a plurality of magnetic pickup coils. Radio frequency (RF) pulses generated by the MRI scanner enable the pickup coils to sense the changes in the energy state of the hydrogen atom protons of the human body. The changes in the energy state of the hydrogen atom protons are then captured, for example, on video images which are subsequently used for diagnostic purposes.

Generally, with respect to the use of MRI scanners, video and audio systems are employed for both (a) clinical and (b) research applications. In clinical applications, the concern is directed to anxious or claustrophobic patients who resist entering the tunnel of the MRI scanner. The capability to adequately display visual information for viewing and to efficiently transmit audio information responsive to the full frequency range of the human ear for listening pleasure are important factors for relief for the anxious or claustrophobic patient. The existing method to achieve patient comfort through visual entertainment is dependent upon the use of liquid crystal display (LCD) projection screens for display of visual information. The existing method to achieve patient comfort through audio entertainment is dependent upon the use of inefficient apparatus that provides poor sound quality and frequency response, is heavy and requires a voltage of approximately (30–50) volts RMS of a received audio signal to generate sufficient sound amplitude to enable the patient to hear the music entertainment over MRI gradient noise.

In one visual entertainment method, the LCD screen contents are viewed by the patient with the assistance of reflecting mirrors. The reflecting mirror method suffers from certain limitations. Initially, the LCD projection screen is located outside the bore of the scanner tunnel. Thus, the position of the patient within the scanner tunnel can interfere with the line of sight to the LCD screen. Further, the level of ambient light within the MRI magnet room and the need for repeated adjustments of the overhead reflecting mirrors result in limited use of this method. Since the overhead reflecting mirrors extend the field of view and the LCD projection screen is outside the tunnel, the patient is aware of her surroundings. Thus, the possibility of being distracted by the external surroundings in addition to the interior of the tunnel further limits the usefulness of this technique for the reduction of anxiety and claustrophobia in patients.

In another visual entertainment method, an MRI video system provides video images in a magnetic field through a fiber optic medium and includes a non-magnetic video source for generating a video image. A composite reduction lens is employed for capturing and compacting the generated video image and a fiber optic bundle receives and transmits the compacted video image. A magnification lens intercepts the compacted video image from the fiber optic bundle and then magnifies and focuses the intercepted video image in a magnetic field. In this application, the LCD image is transmitted to the inside of the scanner tunnel to a set of goggles so that the total field of view of the patient is limited by the goggles.

Current MRI fiber optic systems that position the LCD screen within the scanner room (but outside the bore of the MRI scanner) are extremely useful and provide a definite advance in the art. Notwithstanding, certain features of this design could be improved. In particular, the length of the fiber optic bundle employed to carry the video images from the LCD screen to the eyepiece for viewing by the patient is of concern. As with all transmission systems, a portion of the transmitted parameter is lost during transmission and the longer the transmission path, the greater the loss. For long fiber optic bundles, it is known that the loss of as much as forty percent (40%) of the transmitted video image can occur. This loss affects the resolution and brightness of the transmitted video image. Therefore, the resolution and brightness of the transmitted video image is limited by the length of the fiber optic bundle. Additionally, the longer the fiber optic bundle, the more cumbersome it is to carry the bundle and associated fiber optic equipment into and out of the MRI scanner tunnel.

A fiber optic bundle is comprised of a plurality of optical fibers. When an optical fiber is interrupted, the pixels of light of the transmitted image carried by the interrupted fiber are blocked. This situation results in dead pixels, e.g., black spots that appear on the video display. As the length of the fiber optic bundle is increased, the probability that individual fibers will be broken increases. Further, as the fiber optic bundle is bent and manipulated over a period of time, the number of broken fibers increases. An increasing number of broken fibers results in a greater number of black spots appearing on the video display. Eventually, the transmitted image becomes inadequate and distorted. Thus, long fiber optic bundles are not cost effective.

During an MRI examination, the patient is positioned upon an examination table which can be moved into and out of the MRI scanner tunnel. When lying upon the examination table within the scanner tunnel, the patient's head is positioned within a head coil. The head coil is arranged to surround the patient's head and to provide MRI images thereof. Advanced designs of MRI scanner head coils minimizes the distance between the patient's eyes and the top of the head coil. The limited distance between the patient's head and the head coil would be inadequate to accommodate the goggles employed by known MRI fiber optic systems that (a) position the image from the LCD display within the scanner tunnel or (b) employ a reflecting mirror over the patient's eyes.

The second use of video systems in MRI scanners is directed to research applications. In particular, video systems have been utilized to generate visual activation in MRI scanner studies of the visual cortex in the human brain. The visual activation, also known as functional imaging, typically includes audio or video brain stimulation utilizing computer generated images during an MRI scan of the brain. When, for example, a video image is displayed before the patient during the MRI scans, different sections of the brain will induce energy. The change in the energy level of the brain can be identified on the MRI images. These research activities are typically conducted by universities and research facilities. However, functional imaging is also useful to map specific areas around a tumor in the brain to determine, for example, the boundaries for surgical removal thereof.

The current state of video image display within the MRI magnet room in research applications consists of projection of the image onto a screen mounted on a wall or placed at the end of the imaging table. The projection is achieved within the magnetic environment by employing an MRI-compatible LCD screen. The video information is viewed by the patient with the aid of adjustable light reflecting mirrors. The utility of this method of visual activation is limited by the position of the patient within the scanner tunnel. Further, the level of ambient light in the MRI magnet room will effect the quality of the image that the patient sees on the screen. A high level of ambient light will cause the screen image to be washed out. Also, the time required to adjust the light reflecting mirrors with respect to the LCD screen is determined by the position of the patient inside the scanner tunnel. For functional magnetic resonance imaging, it is ideal to cover the entire patient field-of-view with the MRI screen or display.

The effectiveness of this method of visual activation is further reduced by an open field of view (e.g., the LCD screen is outside of the tunnel) which enables the patient to be aware of her surroundings. During functional imaging, the best results are achieved when the visual stimulus is controlled which is inconsistent with an open field of view. Further, this method of visual activation does not include the ability to generate three-dimensional (3D) images for patient viewing since the image is projected onto a single screen. The inability to create a condition is which the eye and brain perceive a 3D effect prevents virtual reality from being achieved.

It is known that the only reproducible and standard method for visual activation studies has been with the use of goggles fitted with single or multiple light emitting diodes (LEDs). Although this method has been effective in performing feasibility type functional MRI studies of visual activation, it is limited in that it represents a simple two-state photic stimulation paradigm (e.g., a two-state visual stimula). Advanced studies of the visual cortex will require the capability for implementation of visual activation paradigms more sophisticated than simple flashing lights. Further, the limited distance between the patient's head and modern head coil designs would be inadequate to accommodate the goggles employed in visual activation studies.

Typically there are two methods in which audio information can be transmitted to the patient. These methods include the use of (a) a magnetic transducer and (b) a non-magnetic transducer. A magnetic transducer or speaker incorporates a ferrous core in the construction thereof for transducing an electrical signal into sound energy by operating a diaphragm. Because of the ferrous core, the magnetic speaker must be located (20'–50') away from the patient positioned within the tunnel of the MRI scanner. This requirement is necessary so that the static magnetic field of the MRI magnet will not saturate the speaker magnetic core within the transducer and generate heat resulting in damage thereto. The entire magnetic speaker could be attracted and placed in motion by the MRI magnetic field and cause injury to the patient. Positioned at the output of the magnetic speaker is a non-magnetic transmitting medium such as a plastic tube which is employed to deliver the audio signals to a set of headphones used by the MRI patient as is known in the art.

The medium (e.g., plastic tube) utilized to transmit the audio signals from the magnetic speaker to the headphones must also be non-magnetic to avoid generating stray signals that interfere with the MRI magnetic field. Therefore, the plastic tube must be (20'–50') in length extending from the magnetic speaker to the headphones. One of the characteristics of the plastic material used to form the tube is that it tends to absorb the high frequency components of the audio signal. Thus, the frequency response is poor and the sound quality is muffled, unclear and annoying to the MRI patient.

The second method of transmitting audio signals to an MRI patient utilizes a non-magnetic speaker. An example of a non-magnetic speaker includes (a) an electret element or (b) a piezo ceramic (piezoelectric) transducer as is known in the art. These two non-magnetic speakers each serve as a transducer to convert electrical signals to sound energy, do not include a magnetic core and thus do not interfere with the MRI generated magnetic field. The electret element has a plurality of disk-shaped plates and three electrical terminals. The terminals include a positive, negative and biasing terminal. The positive terminal is connected to a first copper plate and the negative terminal is connected to a second copper plate in juxtaposition to the first copper plate. The biasing terminal is connected to a third copper plate positioned between the first and second copper plates. In operation, the positive and negative plates are energized at several hundred volts. A biasing voltage is applied to the third copper plate via the biasing terminal which causes the transducer to oscillate at a frequency within the range of 15 Hz to 30 KHz. The biasing voltage provides the amplification of the audio signal applied to the electret element as is known in the art.

The piezo speaker includes an element shaped in the form of a disk and comprised of, for example, ceramic material. When an audio signal is impressed across a piezo element, the transducer generates sound energy as is known in the art. Further, when a diaphragm is mounted over and communicates with the piezo element, the sound energy is amplified. Each of these transducer structures provides an audio speaker that can be employed to provide audio signals to the MRI patient within the scanner tunnel.

Thus, there is a need in the art for an improvement in combined video and audio systems for use with MRI scanners which provide high resolution video images with a three-dimensional effect, shortens the transmission paths that the video image and audio signals must travel, eliminates the problems associated with fiber optic bundles, is sized to fit within the limited space of modern head coil designs, is light weight and economical to produce, provides audio signals over the full frequency range and can be mounted and operated within the MRI magnetic field.

SUMMARY OF THE INVENTION

The need in the art is addressed by the three-dimensional high resolution magnetic resonance imaging (MRI) video and audio system and method of the present invention. The invention is employed within the magnetic field of a bore of an MRI scanner to provide video images through a relay lens system and corresponding audible sound via a non-magnetic path to an MRI patient and includes non-magnetic video sources and audio speakers for generating the images and sound, respectively. A first non-magnetic shielded generating mechanism is positioned within the magnetic field of the bore for providing a video image. A first optical mechanism captures and transmits the generated video image to provide a high resolution video image. A second optical mechanism magnifies and redirects the high resolution video image for viewing by the patient. A second non-magnetic shielded generating mechanism is positioned within the magnetic field of the bore for providing audible sound over the full frequency range.

In a preferred embodiment, twin optical systems each receive a video signal supplied by a video source to a liquid crystal display (LCD) panel for providing a video image. The video image is impressed upon and travels across a relay lens system to a multi-element eyepiece prism and lens assembly. Each eyepiece assembly utilizes a combination of lenses to magnify the image and a prism to refract the image into the eye of the viewer in the scanner tunnel. Likewise, twin audio systems each receive audio signals supplied by an audio source to a non-magnetic transducer. The audio signals are converted to audible sound over the full frequency range and transmitted to a noise canceling headset via a short non-magnetic path.

DESCRIPTION OF THE INVENTION

Figure 1:
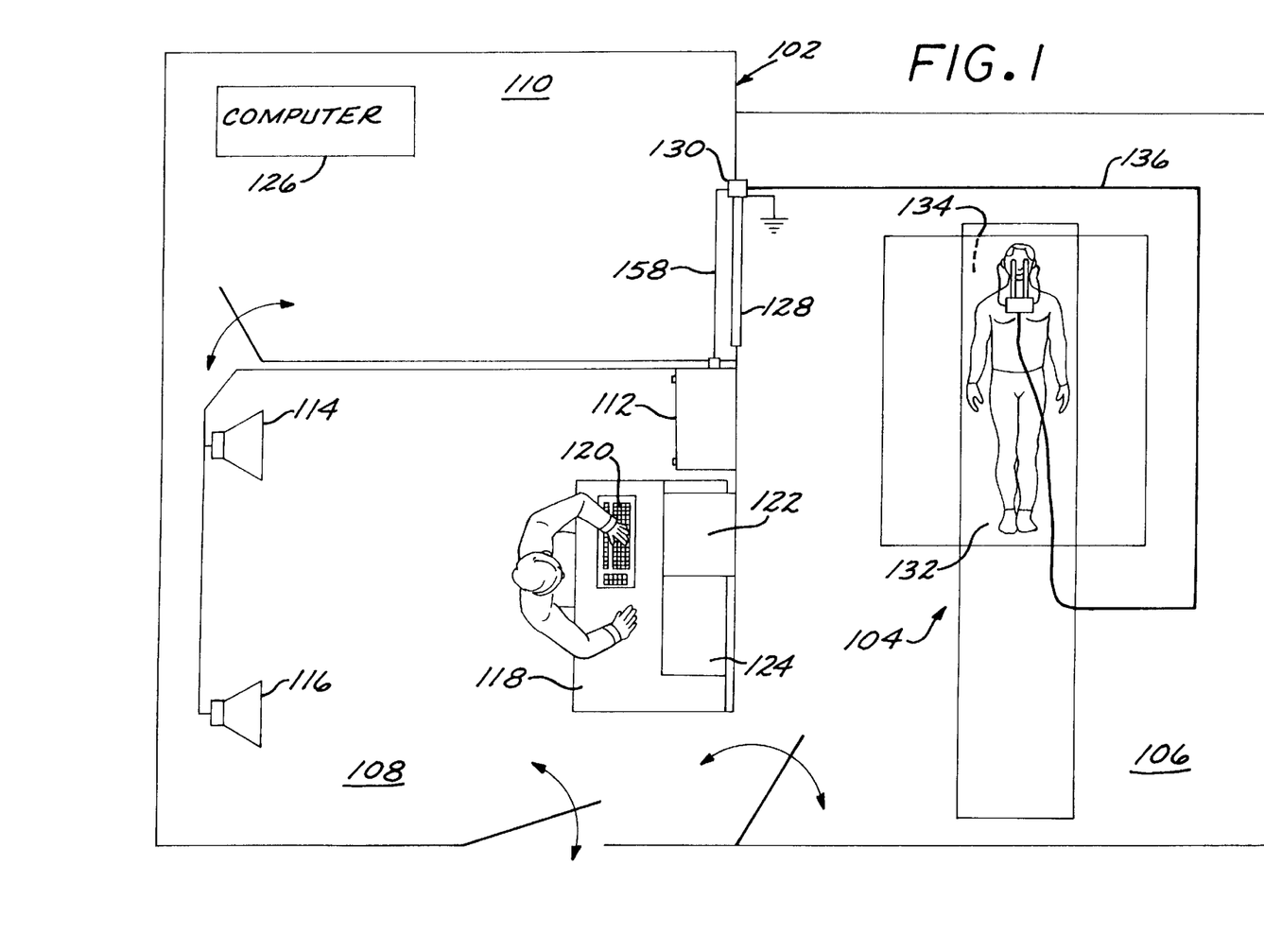
FIG. 1 is a top planar view of an MRI facility including control and computer rooms and an adjoining magnet room housing an MRI scanner.
Figure 2:
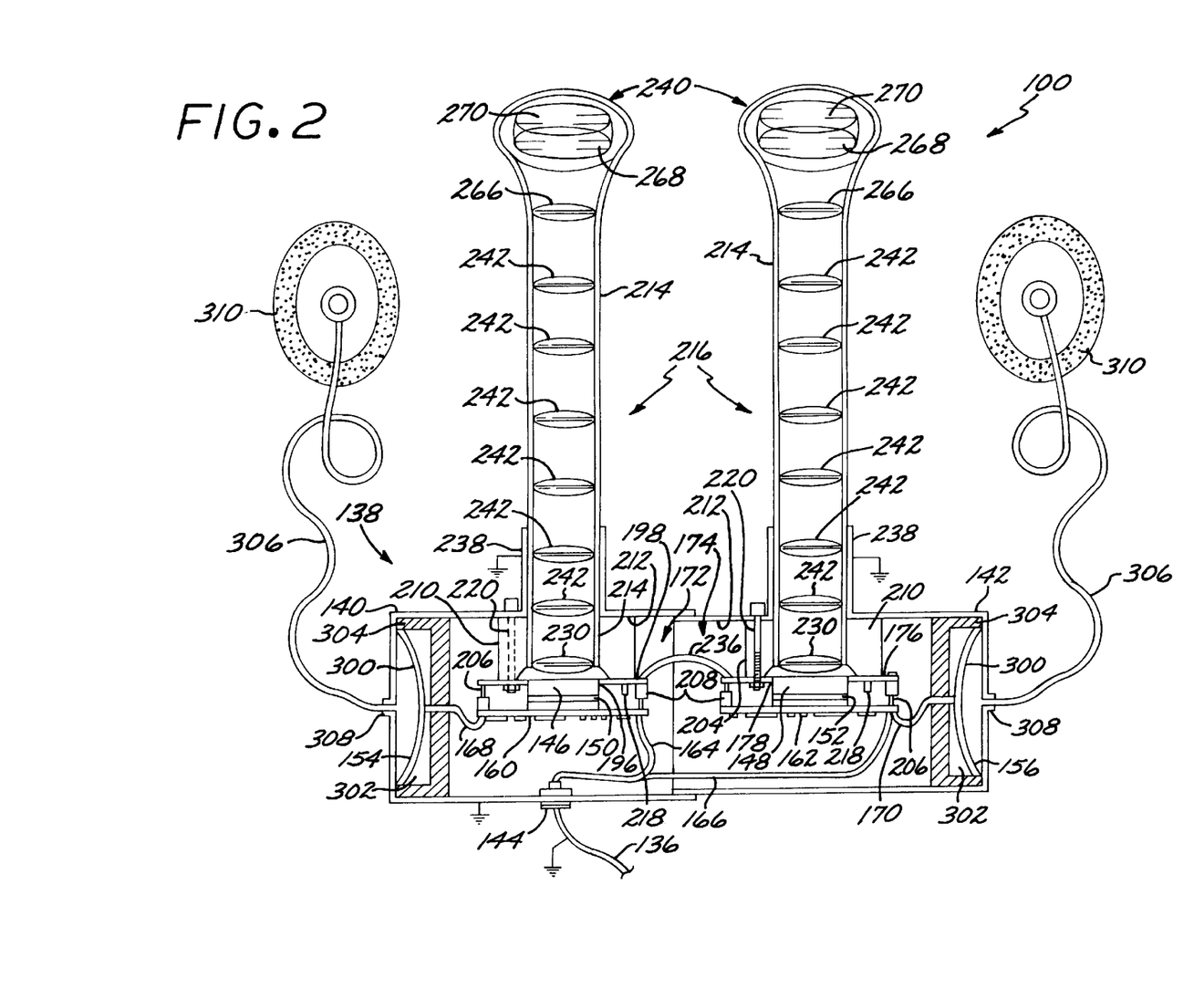
FIG. 2 is a front elevational view partially in cross-section of the three-dimensional high resolution MRI video and audio system of the present invention.

The present invention is a three-dimensional high resolution magnetic resonance imaging (MRI) video and audio system 100 and method as shown in FIG. 2. The MRI video and audio system 100 is utilized to provide a patient undergoing an MRI examination with three-dimensional (3D) high resolution video images and corresponding sound over the full frequency range of the human ear. The patient examination is conducted within an MRI facility 102 which houses an MRI scanner 104 as shown in FIG. 1. The MRI facility 102 includes a magnet room 106, a control room 108 and a computer room 110.

The control room 108 houses an MRI audio/video unit 112 which generates audio and video signals for transmission into the magnet room 106. In electrical communication with the audio/video unit 112 is a pair of loudspeakers 114 and 116 used for receiving voice communications from the patient during the MRI examination. Also included within the control room 108 is a desk 118 for supporting a keyboard 120 and monitor 122 mounted on a shelf 124 for use by an operator during the MRI examination. The computer room 110 houses a computer 126 used in conjunction with the operation of the MRI scanner 104.

The MRI scanner 104 is located within the magnet room 106. Because of the sensitivity of the signals generated by the MRI scanner 104 to electromagnetic interference (EMI) noise, the magnet room 106 must be radio frequency (RF) shielded from the control room 108 and the computer room 110 to prevent the entry of stray RF signals therein. Such shielding is known in the art and prevents interference with the imaging process. Likewise, all electrical and signal facilities entering the magnet room 106 must pass through a penetration panel 128. The penetration panel 128 is electrically grounded to the magnet room 106 and mounted within the wall between the computer room 110 and the magnet room 106 as shown in FIG. 1. Each of the electrical and signal facilities entering the magnet room 106 must also be RF shielded to prevent interference with the imaging process. An adapter 130 is mounted on the penetration panel 128. The adapter 130 is employed to couple the various signal and power conductors that form a shielded cable 136 through the penetration panel 128 and into the magnet room 106. In order to ensure that the magnet room 106 is RF shielded, each of the shielded components of the MRI video and audio system 100 must be interconnected. Thus, the shield of the penetration panel 128 must be connected to the shield of the cable 136.

The magnet room 106 houses the MRI scanner 104 which includes an imaging table 132 on which the patient is placed prior to being moved into a scanner tunnel 134 for the MRI examination. The MRI video and audio system 100 of the present invention is shown conveniently mounted on the chest and head of the patient lying on the imaging table 132 and is connected to the RF shielded cable 136. The shielded cable 136 contains a plurality of conductors including video signal, audio signal and power supply conductors. The audio and video signal conductors of the shielded cable 136 are routed from the MRI audio/video unit 112 within the control room 108 which provides the audio and video signals to the MRI video and audio system 100 as shown in FIG. 1. The power supply conductors which include low voltage direct current and high voltage alternating current (not shown) are routed from the respective power panels (not shown) within the MRI facility 102. Each of the video, audio and power conductors enclosed within the shielded cable 136 are then passed through the penetration panel 128 via the adapter 130.

The video image and sound generating portions of the MRI video and audio system 100 of the present invention are enclosed within a liquid crystal display (LCD) housing 138 as is shown in FIG. 2. The LCD housing 138 is comprised of a pair of adjustable sliding boxes 140 and 142 in which box 142 can be moved into and out of box 140 by applying the appropriate force. Each of the boxes 140 and 142 can be fashioned from, for example, plastic and is coated with a layer of non-ferrous conductive material such as copper or silver. Thus, the LCD housing 138 functions as a Faraday cage. The Faraday cage (e.g., LCD housing 138) isolates (e.g., shields) the electronic components of the MRI video and audio system 100 from the MRI RF pickup coils (not shown) positioned within the bore of the scanner tunnel 134.

The construction of the boxes 140 and 142 is such that the two boxes always remain in physical contact to ensure continuity in the shielding or grounding of the Faraday cage. Further, the layer of non-ferrous conductive material can be positioned over the inner surface or the outer surface or both surfaces of the LCD housing 138. In this manner, any electromagnetic interference (EMI) generated within the LCD housing 138 is intercepted and routed to electrical ground via any of the several shielded ground conductors connected to the LCD housing 138 as shown in FIG. 2. This design prevents the EMI from affecting the quality of the MRI images of the patient and interfering with the video image and sound generating portions of the present invention. Therefore, to ensure the continuity of the RF shield for the magnet room 106, the non-ferrous coating of the Faraday cage (e.g., LCD housing 138) is connected to the shield of the cable 136 which in turn is connected to the shield of the penetration panel 128.

The LCD housing 138 which is utilized in the magnetic field within the bore of the MRI scanner tunnel 134 serves to enclose and protect the video image and sound generating portions of the MRI video and audio system 100. Further, the sliding feature exhibited by boxes 140 and 142 enables the optical and video components of the present invention as described more fully hereinbelow to be adjusted for accommodating the inter-pupil spacing of different users. Additionally, boxes 140 and 142 of the LCD housing 138 can be completely separated to facilitate maintenance to the circuitry contained therein as described hereinbelow.

The shielded cable 136 terminates in the external side of a terminal board connector 144 mounted in the bottom of the LCD housing 138. The terminal board connector 144 is RF shielded by virtue of being connected to the LCD housing 138 (e.g., Faraday cage) and grounded as shown in FIG. 2. The terminated shielded cable 136 includes conductors carrying video signals, audio signals, low voltage d.c. power and high voltage a.c. power. The video conductors can be, for example, standard 75 ohm coaxial video cable while the audio conductors can be standard size 28 AWG wire. The low voltage d.c. power (e.g., 24 vdc) is utilized to energize the video electronic circuitry of a pair of non-magnetic liquid crystal display (LCD) panels 146 and 148 shown in FIGS. 2, 3 and 8. The high voltage a.c. power (e.g., 600 vac) is used to energize a corresponding set of backlights 150 and 152 used in conjunction with the LCD panels 146 and 148, each located within the LCD housing 138.

Both the video and audio signals carried by the shielded cable 136 are supplied by the MRI audio/video unit 112 shown in FIG. 1. The audio portion of the MRI audio/video unit 112 can be supplied by, for example, a stereophonic sound apparatus or other suitable device capable of transmitting appropriate sound signals to a set of non-magnetic audio transducers 154 and 156 located and shielded within the LCD housing 138. The video portion of the MRI audio/video unit 112 can be supplied by, for example, a VCR or other suitable device capable of providing video signals to the pair of LCD panels 146 and 148. It is known that a device that provides a true three-dimensional signal for both the right and left eye is available in the art. The known device is capable of interfacing with an ordinary VCR or personal computer to provide the three-dimensional output signal. The audio and video signals provided by the MRI audio/video unit 112 are carried by a shielded conductor 158 to the adapter 130 mounted on the penetration panel 128 as shown in FIG. 1. Thereafter the audio and video conductors of the shielded conductor 158 pass through the RF shielded adapter 130 and merge with the power supply conductors (not shown) to form the shielded cable 136.

The internal side of the terminal board connector 144 distributes the conductors carrying the video signals, audio signals, a.c. and d.c. power to a pair of main printed circuit boards 160 and 162 via paralleled distribution cables 164 and 166, respectively. Likewise, a pair of audio distribution wires 168 and 170 are shown connecting the main printed circuit boards 160 and 162 to the non-magnetic audio transducers 154 and 156, respectively.

The MRI video and audio system 100 of the present invention is comprised of a pair of LCD assemblies 172 and 174 each enclosed and shielded within the LCD housing 138. The function of the LCD assemblies 172 and 174 is to generate a pair of stereo video images that are viewed by the patient during the MRI examination. The LCD assemblies 172 and 174 are duplicate and thus only LCD assembly 174 will be described in detail with the understanding that LCD assembly 172 is comprised of the same components which operate in the same manner. Thus, LCD assembly 174 is comprised of the non-magnetic LCD panel 148, backlight 152, main printed circuit board 162 and a display panel 176.

Figure 3:
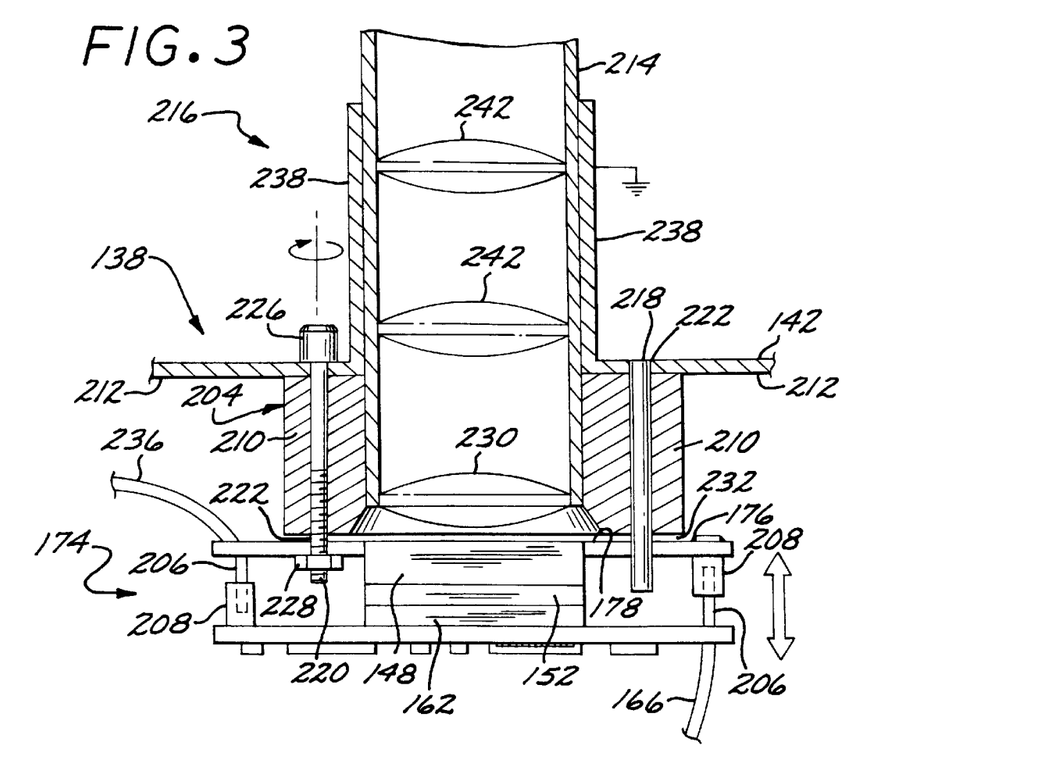
FIG. 3 is a front elevational view partially in cross-section of a focusing adjustment mechanism for use with the three-dimensional high resolution MRI video and audio system of FIG. 2.

The LCD panel 148 is the element of the LCD assembly 174 that generates the video image. The LCD panel 148 is positioned within a penetration 178 formed in the display panel 176 immediately above the backlight 152 as shown in FIGS. 2 and 3. The LCD panel 148 of choice is known in the art and is manufactured and sold under the Part No. LCX003BK by Sony Component Products Company located at 10833 Valley View Street, Cypress, Calif. The LCD panel 148 is a 0.7" diagonal active matrix panel of super thin film polycrystal silicon transistors with built-in drivers. The LCD panel 148 can provide a full color, high resolution display in the NTSC mode (applied in the United States, Canada and Japan). Further, the LCD panel 148 has a density of 103,114 effective pixels and has a typical power consumption of 4 milliwatts. The red, green, blue (R.G.B.) pixels are arranged in a delta pattern to provide high picture quality without the fixed color pattern inherent in vertical strip and mosaic pattern arrangements.

Figures 4, 8A, 8B, 8C:
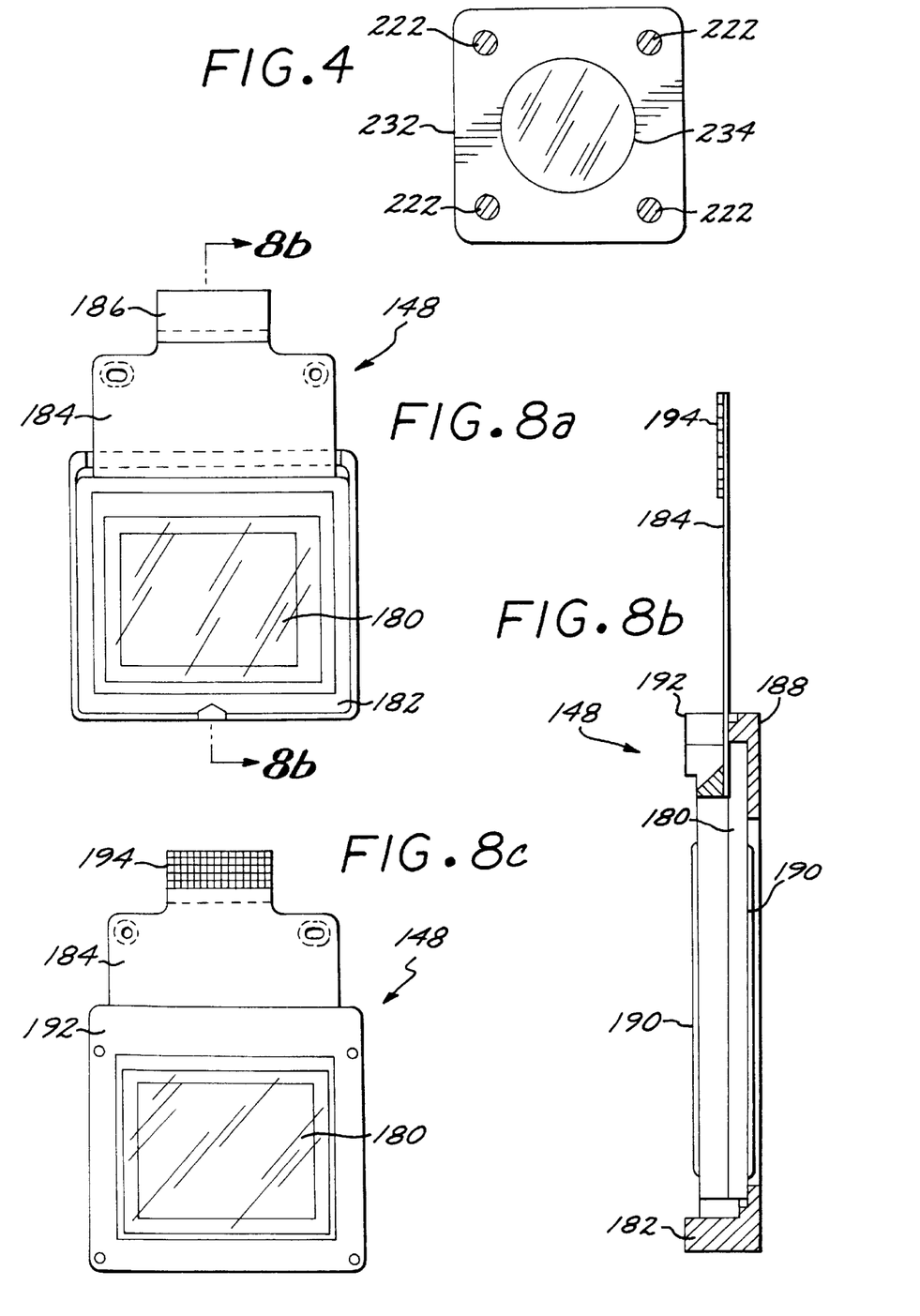
FIG. 4 is a top planar view of an alignment plate for use with the focusing adjustment mechanism of FIG. 3.
FIGS. 8a, 8b and 8c are front, side and rear elevational views, respectively, of a liquid crystal display (LCD) panel used with the three-dimensional high resolution MRI video and audio system of FIG. 2.

An illustration of a suitable LCD panel 148 is shown in FIGS. 8a, 8b and 8c. A front elevational view of the LCD panel 148 is shown in FIG. 8a which clearly shows a display area 180 surrounded by molding material 182. A flux printed circuit board (FPC) area 184 is shown positioned between the molding material 182 and a reinforcing material 186. A side elevational view of the LCD panel 148 taken along line 8b–8b of FIG. 8a is shown in FIG. 8b. Additional components of the LCD panel 148 shown in FIG. 8b include reinforcing material 188 and a pair of polarizing plates 190. FIG. 8c shows a back elevational view of the LCD panel 148 and further illustrates an outside frame 192 and a pin connection pad 194. Each of the components illustrated in FIGS. 8a, 8b and 8c are known in the art and available in Sony Part No. LCX003BK. It is noted that LCD panel 146 shown in FIG. 2 is mounted within a penetration 196 of a display panel 198 and functions in the same manner as LCD panel 148.

Mounted immediately beneath the LCD panel 148 is the backlight 152. The backlight 152 is a high voltage, cold cathode florescent (CCF) lamp which is an integral part of the LCD panel 148. The operating parameters of the backlight 152 include an operating terminal voltage of approximately 600 volts a.c. and a line amperage of 15 milliamps that operates at a frequency in the kilohertz range. The power supply (not shown) of the backlight 152 utilizes a step-up transformer that includes a core comprised of ferrous material. Ferrous material will not operate properly when positioned within the MRI magnetic field. Therefore, the power supply for the backlight 152 must be located remote from the MRI scanner tunnel 134. Further, the magnetic field associated with the power supply of the backlight 152 must have a field strength of less than thirty Gauss. In addition, there can be no ferrous material located within any components of the MRI video and audio system 100 including the main printed circuit boards 160 and 162 as shown in FIGS. 2 and 3. The description of backlight 152 applies equally to backlight 150 associated with the LCD panel 146.

Mounted directly beneath the backlight 152 is the main printed circuit board (PCB) 162 as shown in FIG. 2. The main PCB 162 includes all of the electronic circuitry associated with the LCD panel 148 and is utilized in conjunction with the display panel 176 to sandwich the LCD panel 148 and the backlight 152. The main PCB 162 is more clearly shown in FIG. 7 which is a block diagram of the three major components each of which are known in the art. The three major components include a decoder/signal driver 200, a timing generator/pulse driver 202 and the LCD panel 148.

Figure 7:
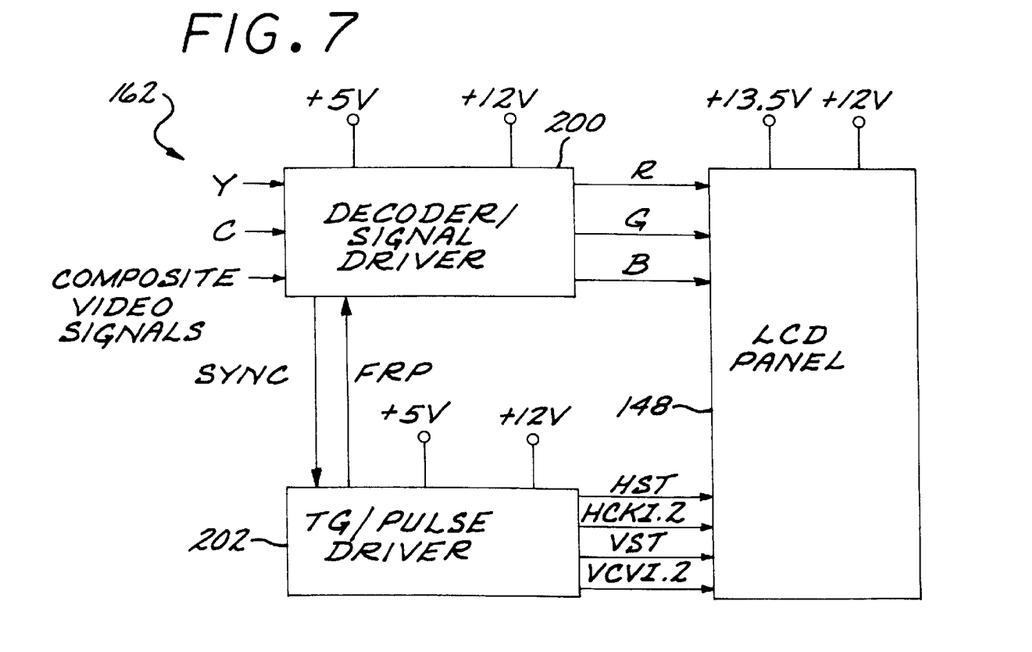
FIG. 7 is a block diagram of the color display system of the three-dimensional high resolution MRI video and audio system of FIG. 2.

The decoder/signal driver 200 is an integrated circuit designed to drive the LCD panel 148 and which receives both a +5 volt and +12 volt input. The decoder portion converts the composite video signals into red, green, blue (R.G.B.) signals for the LCD panel 148. The signal driver portion delivers the R.G.B. signals to the LCD panel 148. The timing generator/pulse driver 202 also receives both a +5 volt and +12 volt input. The timing signal generator portion develops a timing signal or pulse to drive the pixels of the LCD panel 148 while the pulse driver portion delivers the (horizontal and vertical) timing signals (HST, HCKI.2, VST, VCKI.2) to the LCD panel 148. Further, the decoder/signal driver 200 and the timing generator/pulse driver 202 exchange input signals (e.g., sync and FRP signals) as shown in FIG. 7.

The LCD panel 148 receives the R.B.G. signals from the decoder/signal driver 200 and the horizontal and vertical timing signals from the timing generator/pulse driver 202 to display the video image within the magnetic field without affecting the MRI image quality. The LCD panel 148 also receives +13.5 volt and +12 volt inputs. Examples of suitable devices for use in the design of the main PCB 162 are as follows. Sony Part No. CXA1785R is a decoder and signal driver which converts composite video signals into R.G.B. signals before they are transmitted to the LCD panel 148. Sony Part No. CXD2403R is a timing generator and pulse driver that synchronizes the timing of the color signals and generates horizontal and vertical signals. The LCD panel 148 can be comprised of Sony Part No. LCX003BK for use with NTSC video signals. The entire circuit for the main PCB 162 is disclosed in a Sony drawing having reference number LCD005-1. The design and operation of each of the components of the main PCB 160 are duplicate to those described above for the main PCB 162.

The display panel 176 serves to interface with the LCD panel 148, act as a mounting platform for certain of the electronic components of the main PCB 162 and to interface with a focusing adjustment mechanism 204. The penetration 178 formed within the display panel 176 as shown in FIG. 2 serves as a window in which the display area 180 of the LCD panel 148 can be viewed. The LCD panel 148 must be mounted within the penetration 178 so that when the image is viewed through an optical subsystem, the image will appear in the upright position. Also, by utilizing the display panel 176 to mount components associated with the main PCB 162, the LCD assembly 174 can be miniaturized.

It is noted that the LCD panel 148 and the backlight 152 are sandwiched between the main PCB 162 and the display panel 176. In particular, FIGS. 2 and 3 show that the main PCB 162, the backlight 152, the LCD panel 148 and the display panel 176 are connected as a single unit within the LCD housing 138. This is accomplished by utilizing eight pin PC mount male-female connectors to join or jump the main PCB 162 with the display panel 176. The male-female connectors comprise male connectors 206 and female connectors 208 as best shown in FIG. 3. This design provides mechanical support to each of the four components enabling the LCD assembly 174 to move in unison. Further, mounting of the main PCB 162, the backlight 152, the LCD panel 148 and the display panel 176 as a single unit provides the added benefits of keeping the LCD assembly 174 dark and free of any contamination in case the LCD housing 138 is opened for maintenance.

By inspection of FIGS. 2 and 3, it can be seen that the focusing adjustment mechanism 204 includes a non-ferrous mounting bracket 210 which butts against the top inside surface 212 of the LCD housing 138 and surrounds a lens housing 214. The mounting bracket 210 is fixedly connected to the top inside surface 212 and the lens housing 214 by either being integrally molded thereto as by being comprised of plastic or by being adhered with an adhesive.

The focusing adjustment mechanism 204 is designed to permit the position of the LCD assembly 174 to be moved slightly with respect to the LCD housing 138 to adjust the focal point of an optical relay lens system 216 for different users. The focusing adjustment mechanism 204 includes a set of four shafts of which three shafts 218 have a smooth outer surface and one shaft 220 is threaded as is shown in FIG. 3. Each of the shafts 218 and 220 fit into a smooth bore 222 formed in the mounting bracket 210 as shown in FIG. 4. At the top of the threaded shaft 220 is a knob 226 which enables the threaded shaft 220 to be manually rotated within the corresponding bore 222. Each of the shafts 218 and 220 extend through the mounting bracket 210 and the display panel 176. The threaded shaft 220 is received by a threaded nut 228 which can be physically attached to the bottom of the display panel 176 as with an adhesive.

Each of the shafts 218 and 220 extends through the corresponding bore 222 of the mounting bracket 210 and the top inside surface 212 of the LCD housing 138. The non-threaded shafts 218 are employed for alignment purposes and prevent the image on the LCD panel 148 from rotating in the horizontal plane. The focusing knob 226 is mounted to the top of the threaded shaft 220 and is large enough to avoid passing through the bore 222 as shown in FIG. 3. Mounted beneath the optical relay lens system 216 and a focus lens 230 but above the display panel 176 is an alignment bracket 232 as shown in FIG. 4. The alignment bracket 232 shows the four bores 222 which receive the shafts 218 and 220, respectively. The smooth bores 222 ride on the non-threaded shafts 218 and on the threaded shaft 220. A center penetration 234 is formed at the center of the alignment bracket 232 which is aligned with the penetration 178 formed in the display panel 176. The pair of penetrations 178 and 234 enable the focus lens 230 to capture the entire video image appearing on the LCD panel 148 mounted directly beneath and to focus the image through the optical lens relay system 216.

When the knob 226 is manually rotated, the threaded shaft 220 rotates within the smooth bore 222. The threaded shaft 220 does not advance or retract within the smooth bore 222 because there are no threads within the smooth bore 222. However, the threads of the shaft 220 do turn in the corresponding threads of the stationary threaded nut 228. Thus, the threaded nut 228 does advance and retract along the threads of the shaft 220 when the threaded shaft 220 is manually rotated. The direction of movement of the threaded shaft 220 and the threaded nut 228 depends upon the direction of rotation of the knob 226. Movement of the threaded nut 228 along the threaded shaft 220 carries with it the entire LCD assembly 174 and thus permits the distance between the LCD panel 148 and the focus lens 230 to be adjusted. The adjusted distance is sufficient to alter the focal point of the optical relay lens system 216.

In order to obtain a 3D effect with the MRI video and audio system 100, each video signal delivered to the respective LCD panels 146 and 148 must originate from a separate video source such as a VCR, computer or the like. In the alternative, any suitable video source can be interfaced with known devices that provide a three-dimensional signal for both eyes of the patient. If a condition should arise that a 3D stereo effect is not required, the signals can be provided by a single video source to provide mono-operation. Under these conditions, the main PCB 162 of LCD assembly 174 is sufficient to provide the video and audio signals and power supply to both LCD panels 146 and 148. In practice, this is accomplished by using a parallel ribbon cable 236 to link the display panel 176 of LCD assembly 174 to display panel 198 of LCD assembly 172. In this manner, the audio and video signals and the power supply are shared to provide a mono effect.

The LCD housing 138 includes an upward extension 238 which lies in the same plane as the mounting bracket 210 of the focusing adjustment mechanism 204 best shown in FIG. 3. The upward extension 238 is attached to the lens housing 214 as with an adhesive for providing support to the optical relay lens system 216. The upward extension 238 is part of the Faraday cage and is thus shielded by being connected to electrical ground.

The function of the optical relay lens system 216 is to transfer the video image generated by the LCD panel 148 to an eyepiece 240 for viewing by the patient. It is noted that the optical relay lens system 216 such as the one utilized in the present invention is known in the art. In FIG. 2, the optical relay lens system 216 is illustrated by a general diagram that shows the lens housing 214 enclosing a plurality of lenses 242. The number of lenses 242 can vary depending upon the length of the lens housing 214 and the correction required for the aberration which is the distortion of the image through the lenses 242. The more lenses 242 included in the lens housing 214, the more the distortion of the image can be minimized.

Figure 5:
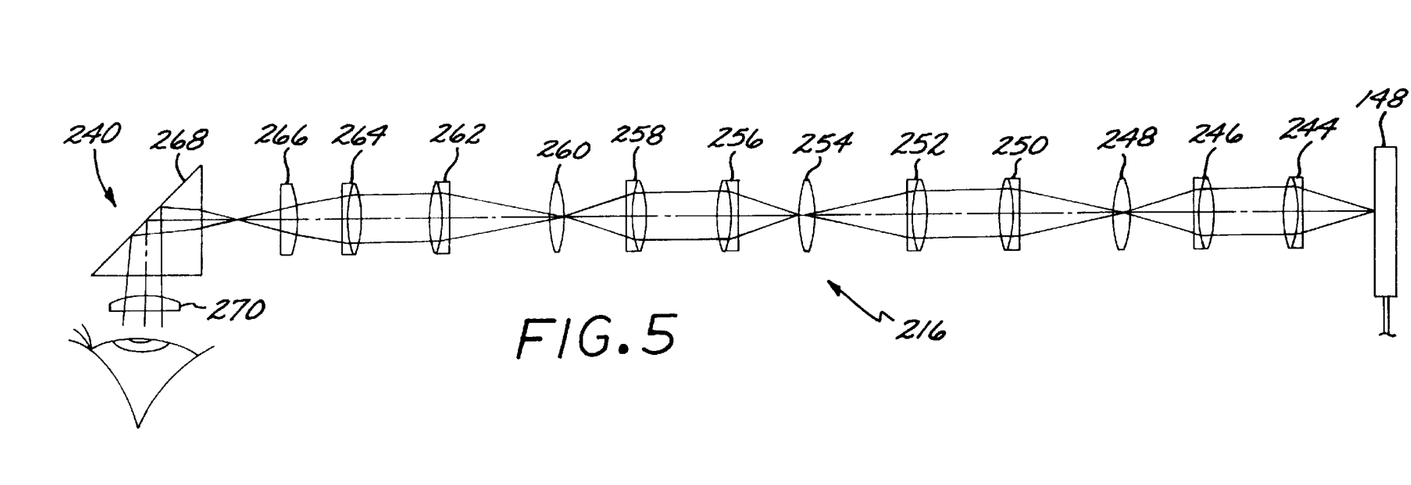
FIG. 5 is a schematic diagram of an optical relay lens system for use with the three-dimensional high resolution MRI video and audio system of FIG. 2.

A more detailed diagram of the optical relay lens system 216 is shown in FIG. 5. The number of lens combinations shown in FIG. 5 of the optical relay lens system 216 is equal to the number of lenses 242 shown enclosed within the lens housing 214 of FIG. 2. The LCD panel 148 is shown located at the entry of the optical relay lens system 216 in FIG. 5. The first combination of two lenses 244 and 246 is equivalent to the focus lens 230 shown in FIG. 2. The combination of lenses 244 and 246 serve to maintain the light from the LCD image in a collimated condition, e.g., maintain the light rays in a parallel state so that a particular pixel appearing on the LCD screen at a first position also appears at the first position on the transmitted image in the eyepiece 240 as perceived by the patient.

The next lens 248 shown on FIG. 5 is equivalent to the next lens 242 as shown on FIG. 2. Lens 248 serves to reverse the image and couple the collimated light rays exiting lens 246 to the next combination of lenses 250 and 252. Lenses 250 and 252 serve the same function as lenses 244 and 246. Thereafter, a lens 254 serves the same function as the coupler lens 248 and so on with each stage functioning as an optical relay using combinations of lenses equivalent to lens 242 shown in FIG. 2. Likewise, lenses 256 and 258 and lens 262 and 264 each serve as optical relays collimating the light rays of the LCD image and lens 260 serves as an optical coupler as with lenses 254 and 248. The final lens in the optical relay lens system 216 is a magnification lens 266 used to magnify and focus the video image received from the LCD panel 148.

The combination of lenses used in the optical relay lens system 216 has been commonly used in related fields of industrial technology including but not limited to laparoscopy (viewing stomach interior during surgery), endoscopy (viewing joint interior during surgery) and borescopy (viewing interior of gun barrel). The optical relay lens system 216 can be custom designed for a particular application. In the alternative, off-the-shelf designs are available from COMEG U.S.A. located at 1200 South Parker in Denver, Colo. and from Edmund Scientific Company located at 101 E. Gloucester Pike in Barrington, N.J. 08007-1380.

The optical relay lens system 216 terminates in a right angle prism 268 which receives the magnified video image from magnification lens 266. The size of the video image depends upon the magnification factor of the lens 266. The function of the right angle prism 268 is to refract the light orthogonally (e.g., at a right angle) into the eyepiece 240 to enable the patient to see a virtual image as if the image were projected onto a large screen. A second magnification lens 270 receives the refracted light rays from the prism 268 and magnifies and focuses the video image prior to perception by the eye of the patient. Both of the magnification lenses 266 and 270 are normally attached to the right angle prism 268 as with an adhesive. The right angle prism 268 and the associated lenses 266 and 270 are also available from Edmund Scientific Company. The optical relay lens system as disclosed in FIG. 5 is suitable for use in the manufacture of small quantities as a prototype to carry the video image from the LCD panel 148 to the eyepiece 240.

Figure 6:
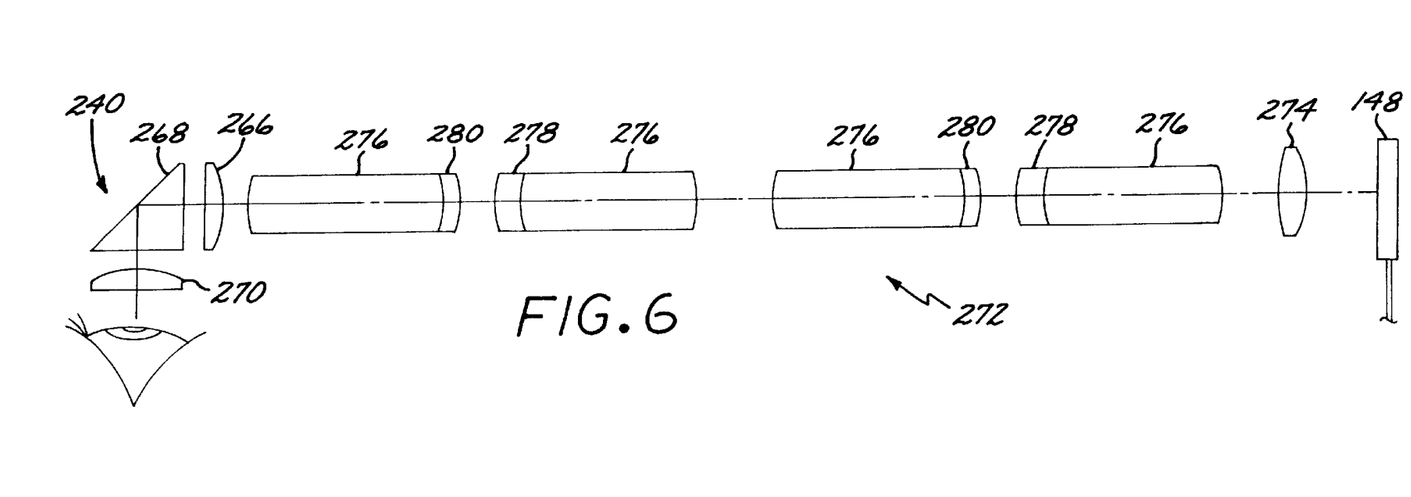
FIG. 6 is a schematic diagram of a rod lens relay system for use with the three-dimensional high resolution MRI video and audio system of FIG. 2.

An alternative optical relay system for use in transmitting the video image to the eyepiece 240 and suitable for mass production is disclosed in FIG. 6 and comprises a rod lens relay system 272. The video image which is provided by the LCD panel 148 is projected onto an objective lens 274. The objective lens 274 serves as a focus lens and operates in conjunction with the focusing adjustment mechanism 204. The rod lens relay system 272 is comprised of a plurality of optical unit rods 276 each including a doublet achromatic lens 278 (e.g., two lenses) and a single lens 280 on the opposing side. Use of the doublet achromatic lens 278 and the single lens 280 is known in the art. As with the optical relay lens system 216, the combination of lenses of the rod lens relay system 272 is utilized to collimate the light of the video image (e.g., to make the light rays parallel). This design corrects for achromatic aberration (where the edges of the image are distorted) as is known in the art.

The number of optical unit rods 276 (e.g., doublets 278 and single lens 280) required in the design of the rod lens relay system 272 in a particular application is determined by the distance between the LCD panel 148 and the optical eyepiece 240. The rod lens relay system 272 is also available from COMEG U.S.A. in Denver, Colo. An expensive precision design mold is required to develop the rod lens relay system 272. However, subsequent mass production of the rod lens relay system 272 is more economical than for the optical relay lens system 216. The eyepiece 240 comprised of the right angle prism 268 and the first and second magnifying lens 266 and 270 are exactly duplicate to and operate the same as those described in conjunction with the optical relay lens system 216.

Several advantages are derived from employing either the optical relay lens system 216 or the rod lens relay system 272 to transmit the video image from the LCD panel 148 to the eyepiece 240 as opposed to a fiber optic bundle. There are no dead pixels and thus the video images are very clear as with a camera lens. The lens relay system is many times more economical than a fiber optic bundle or rod. The relay lens system is lighter in weight which is important since the MRI video and audio system 100 is mounted over the patient's face. Additionally, the relay lens system is compatible with advance technology in that it will still be viable as a circuit element when the resolution of the LCD panel 148 increases. Notwithstanding these advantages, it is to be understood that either the optical relay lens system 216 or the rod lens relay system 272 can be replaced by a fiber optic rod (not shown). However, the fiber optic rod is expensive, heavy and exhibits limited resolution and thus either of the two lens relay systems are preferred.

A description of the audio portion of the MRI video and audio system 100 will now be presented. The audio portion is comprised of a high efficiency, full frequency response MRI non-magnetic transducer which converts audio signals into sound energy. A non-magnetic transducer 300 is shown mounted and shielded within each end of the LCD housing 138 in FIG. 2. Both non-magnetic shielded transducers 300 are duplicate copies and thus only one will be described in detail. The non-magnetic shielded transducer 300 does not have a magnetic core and thus can be successfully operated within the MRI magnetic field. In order to direct the generated sound energy to the patient, the transducer 300 is enclosed in a pocket 302 comprised of noise absorbing material 304 which isolates the transducer 300 from the video section of the MRI video and audio system 100. The sound absorbing material 304 can be, for example, any lightweight material suitable for trapping sound such as paper particles, fiberglass or the like.

The audio distribution wires 168 and 170 are shown in FIG. 2 transporting audio signals from the parallel distribution cables 164 and 166 via the main PCBs 160 and 162, respectively. The audio signals are transmitted to the non-magnetic shielded transducer 300 for conversion to sound energy. The sound energy is amplified by the transducer 300 and thereafter transmitted to a non-magnetic tube 306 which serves as a conduit. The non-magnetic tube 306 is approximately 8' in length and ¼" in diameter and can be comprised of plastic as is known in the art. It is noted that the short length of plastic tube 306 minimizes the loss of high frequencies (e.g., provides a high frequency response) and providing a clear sound having high fidelity characteristics.

The respective ends of the LCD housing 138 each include a nipple formation 308 which receives the end of the plastic tube 306. This connection provides a direct pathway for the sound energy to travel from the transducer 300 to the plastic tube 306. The plastic tube 306 transports the sound energy to a noise canceling headset 310 as is shown in FIG. 1. A suitable noise canceling headset for use in the present invention is shown and described in copending patent application having Ser. No. 07/653,711 and filed on Feb. 11, 1991 by the present applicant. The copending application is entitled Magnetic Resonance Imaging Compatible Audio and Video System.

Several non-magnetic transducers known in the art are suitable for use as the non-magnetic shielded transducer 300 of the present invention. For example, a piezoelectric transducer would be appropriate for the present application. An example of a suitable piezoelectric transducer is shown and described in a copending patent application having Ser. No. 08/221,852 and filed on Apr. 1, 1994 by the present applicant. The title of the copending application relating to piezoelectric transducers is High Efficiency Full Frequency Response MRI Audio Transducer System and Method.

Figures 9, 10:
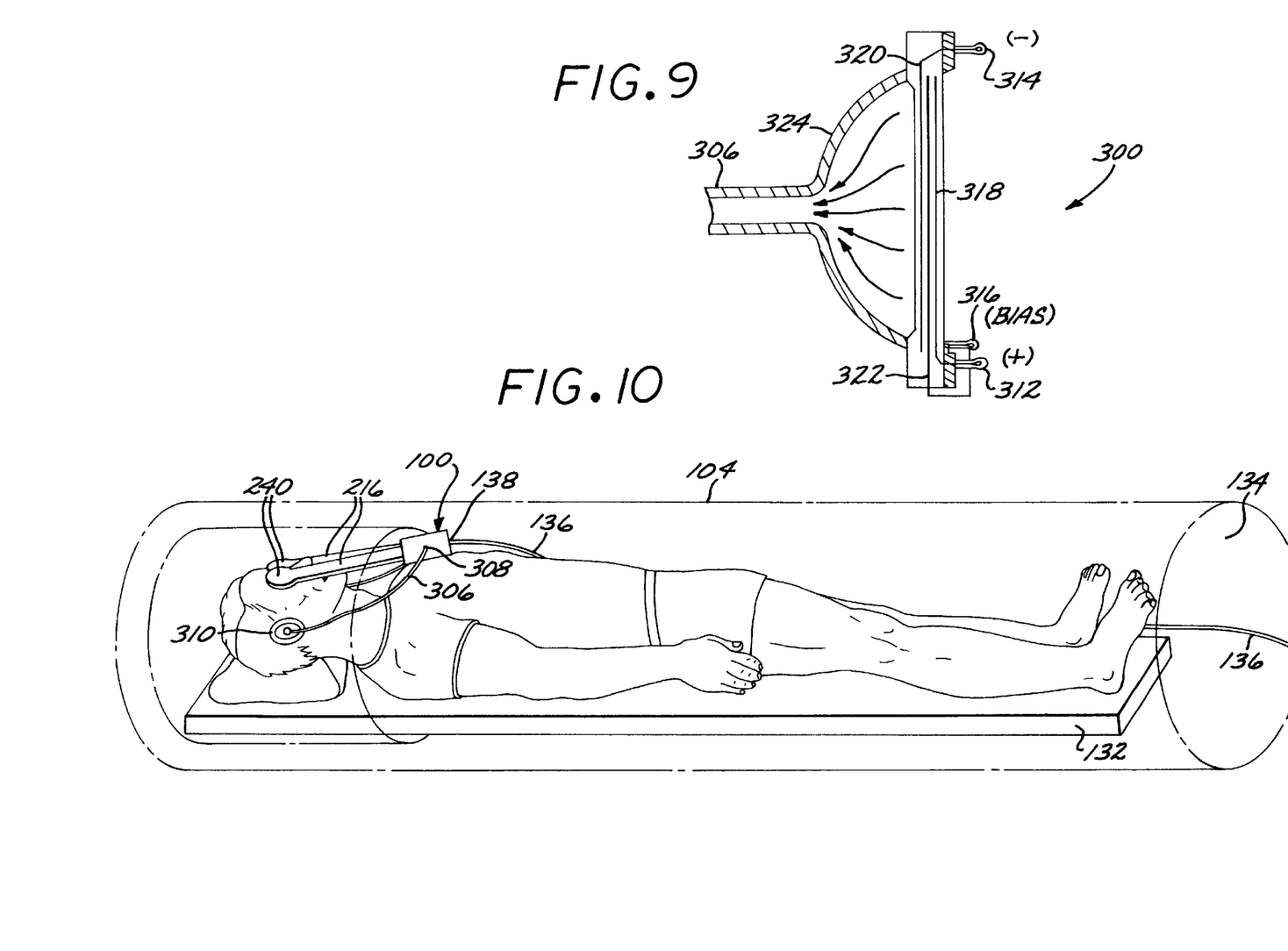
FIG. 9 is a cross-sectional view of the audio section of the three-dimensional high resolution MRI video and audio system of FIG. 2 showing a non-magnetic transducer and sound collection hood.
FIG. 10 is a perspective view of a patient positioned within the body coil of an MRI scanner tunnel showing the three-dimensional high resolution MRI video and audio system of FIG. 2 positioned on the chest of the patient.

Another non-magnetic transducer suitable for use in the present invention is the electret element shown in FIG. 9. The non-magnetic electret element 300 serves to convert electrical signals to sound energy, does not include a magnetic core and thus does not interfere with the MRI generated magnetic field. The electret element 300 has a plurality of disk-shaped plates and three electrical terminals. The electret element 300 includes a positive terminal 312, a negative terminal 314 and a biasing terminal 316. The positive terminal 312 is connected to a first copper plate 318 and the negative terminal 314 is connected to a second copper plate 320 in juxtaposition to the first copper plate 318. The biasing terminal 316 is connected to a third copper plate 322 positioned between the first and second copper plates 318 and 320, respectively.

In operation, the first (+) and second (−) copper plates 318 and 320 are energized at several hundred volts. A biasing voltage of 150–200 volts is applied to the third copper plate 322 via the biasing terminal 316 which causes the transducer 300 to oscillate at a frequency within the range of 15 Hz to 30 KHz. The biasing voltage provides the amplification of the audio signal applied to the electret element 300 as is known in the art. The amplified sound energy provided by the transducer 300 shown in FIG. 9 is collected by a sound collection hood 324 and routed into the non-magnetic tube 306 for transmission to the headset 310. The electret element serving as the transducer 300 is available from STAX Kogyo, Inc. located at 16920 Halldale Avenue, Gardena, Calif. 90247 under the Part No. SR-5N.

The patient is shown in the supine position during an MRI examination in FIG. 10 with the LCD housing 138 of the three-dimension high resolution MRI video and audio system 100 mounted on his chest. The eyepiece 240 is positioned over the eyes of the patient and the headset 310 is mounted over his ears. The shielded cable 136 is shown running through the scanner tunnel 134 from the penetration panel 128 (shown in FIG. 1) to the LCD housing 138. An additional feature includes installing a mercury on-off switch (not shown) within the LCD housing 138 to facilitate energizing the video portion of the MRI video and audio system 100. The mercury switch (not shown) can be strategically placed and wired so that the video portion would be energized only when the LCD housing 138 was in the horizontal position.

It is noted that a novel feature of the present invention is that all of the components of the MRI video and audio system 100 are utilized in the magnetic field of the bore of the MRI scanner 104. It is emphasized that the present invention operates properly while positioned in the bore of the MRI scanner because the LCD housing 138 is a Faraday cage which shields each of the electronic components contained therein, the components of the main PCBs 160 and 162 are of non-ferrous construction, and all components containing ferrous construction are located remote from the magnetic field of the MRI scanner 104. However, it should be emphasized that the main PCBs 160 and 162 can be located outside of the magnetic field of the scanner tunnel 134 with the optics and the LCD panel 148 located within the magnetic field and the invention would operate in a manner equivalent to that described hereinabove.

The present invention provides novel advantages over other video and audio systems known in the art. The invention is a combined video and audio system, the set-up time of the invention is reduced, the set-up mirror is eliminated, the field of view from inside the scanner tunnel 134 is limited, all system components are located within the bore of the MRI scanner tunnel, the video and audio transmission paths are shorter, the fiber optic bundle/rod is eliminated, the new video and audio system fits inside the headcoil within the scanner tunnel 134, the use of the Faraday cage eliminates the need for a low pass filter, and installation is simple and economical.

While the present invention is described herein with reference to illustrative embodiments for particular applications, it should be understood that the invention is not limited thereto. Those having ordinary skill in the art and access to the teachings provided herein will recognize additional modifications, applications and embodiments within the scope thereof and additional fields in which the present invention would be of significant utility.

It is therefore intended by the appended claims to cover any and all such modifications, applications and embodiments within the scope of the present invention. Accordingly,

What is claimed is:

1. An image generating system for use within a magnetic field of a scanner tunnel of a magnetic resonance imaging scanner, comprising:

a first non-magnetic image generator disposed within said scanner tunnel for generating a visible image in response to first electronic image-defining signals, said first image generator comprising a first electronic display device responsive to said first image-defining signals;

a non-magnetic, non-ferrous shield enclosure for housing said first non-magnetic image generator within said scanner tunnel and within a strong magnetic field generated within said scanner tunnel during imaging operation of said imaging scanner, said shield enclosure adapted to shield said image generator from RF pulses generated by said imaging scanner during imaging operation such that said RF pulses do not appreciably affect operation of said first image generator, said shield enclosure further adapted to shield said imaging scanner from any electromagnetic interference generated by said first image generator such that said first image generator does not appreciably affect operation of said imaging scanner; and first optical apparatus connected to said shield enclosure for directing said visible image from a penetration in said shield enclosure to a person's eye for viewing by a person disposed within said scanner tunnel.

2. The system of claim 1 wherein said shield enclosure is adapted to perform the function of a Faraday cage.

3. The system of claim 1 wherein said first electronic display device comprises a liquid crystal display.

4. The system of claim 3 wherein said liquid crystal display (LCD) comprises a display panel having a penetration formed therein, and a non-magnetic LCD panel for generating a video image positioned within said penetration, and wherein said shield enclosure further includes a supporting bracket for supporting said first optical apparatus in alignment with said penetration.

5. The system of claim 4 wherein said first optical apparatus comprises an optical lens relay system including a focal lens.

6. The system of claim 4 wherein said LCD includes a printed circuit board disposed within said shield enclosure, and wherein said image generator is free of any ferrous material.

7. The system of claim 4 wherein said LCD further includes a high voltage backlight disposed beneath said display panel and within said shield enclosure.

8. The system of claim 7 wherein said backlight includes a cold cathode fluorescent lamp, and further comprising a step-up transformer located remote from the MRI scanner tunnel.

9. The system of claim 1 wherein said first optical apparatus comprises an optical relay lens system.

10. The system of claim 1 wherein said first optical apparatus comprises a rod lens relay system.

11. The system of claim 1 wherein said first optical apparatus comprises an eyepiece including at least one magnifying lens for magnifying said image.

12. The system of claim 11 wherein said eyepiece comprises a prism for orthogonally redirecting said image.

13. The system of claim 1 wherein said shield enclosure comprises apparatus for adjusting to accommodate interpupil spacing variations of different persons within the scanner tunnel.

14. The system of claim 1 wherein said first optical apparatus includes a focus lens for focusing said generated image.

15. The system of claim 14 further including a focusing adjustment mechanism for changing the distance between said focusing lens and said image generator.

16. The system of claim 15 wherein said focusing adjustment mechanism includes an alignment plate for preventing lateral movement of said image generator.

17. The system of claim 1 wherein said first image generator comprises a video image generator and said first electronic image-defining signals include video image signals.

18. The system of claim 1 wherein said shield enclosure comprises first and second non-magnetic sliding boxes comprising electrically conductive surfaces, said first box adapted for movement into and out of said second box.

19. The system of claim 1 further comprising a second non-magnetic image generator disposed within said scanner tunnel for generating a second visible image in response to second electronic image-defining signals, said second image generator comprising a second electronic display device responsive to said second image-defining signals, said second display device disposed within said shield enclosure, and a second optical apparatus for directing said second visible image for viewing by said person, and wherein said first image generator and said first optical apparatus cooperate to direct said first image for viewing by the right eye of said person, and said second image generator and said second optical apparatus cooperate to direct said second image for viewing by the left eye of said person, thereby providing a binocular image generating system.

20. The system of claim 1 wherein said first electronic image-defining signals are carried via a non-magnetic, RF-shielded cable extending into said scanner tunnel and connected into said shield enclosure.

21. The system of claim 1 wherein said first display device comprises a liquid crystal display, and a backlight powered by a remote source located outside said scanner tunnel, said remote source connected to said shield enclosure via a non-magnetic, RF-shielded cable.

22. The system of claim 1 further comprising a non-magnetic audio generator responsive to electrical audio-defining signals for generating audio signals, said audio generator disposed within said shield enclosure.

23. The system of claim 22 wherein said audio generator comprises a non-magnetic transducer.

24. The system of claim 22 wherein said audio generator comprises a non-magnetic tube for transmitting said audio signals to a headset.

25. An image generating system for use within a magnetic field of a scanner tunnel of a magnetic resonance imaging scanner, comprising:

a first non-magnetic image generator disposed within said scanner tunnel for generating a visible image in response to first electronic image-defining signals, said first image generator comprising a first electronic display device responsive to said first image-defining signals;

a second non-magnetic image generator disposed within said scanner tunnel for generating a second visible image in response to second electronic image-defining signals, said second image generator comprising a second electronic display device responsive to said second image-defining signals;

a non-magnetic, non-ferrous shield enclosure for housing said first and second non-magnetic image generators within said scanner tunnel and within a strong magnetic field generated within said scanner tunnel during imaging operation of said imaging scanner, said shield enclosure for shielding said image generators from RF pulses generated by said imaging scanner during imaging operation such that said RF pulses do not appreciably affect operation of said image generators, and for shielding said imaging scanner from any electromagnetic interference generated by said image generators such that said image generators do not appreciably affect operation of said imaging scanner;

first optical apparatus for directing said first visible image for viewing by a person disposed within said scanner tunnel;

second optical apparatus for directing said second visible image for viewing by said person; and wherein said first image generator and said first optical apparatus cooperate to direct said first image for viewing by the right eye of said person, and said second image generator and said second optical apparatus cooperate to direct said second image for viewing by the left eye of said person; and wherein said shield enclosure comprises first and second non-magnetic sliding boxes, said first box adapted for movement into and out of said second box so as to accommodate inter-pupil spacing variations of different persons within the scanner tunnel.

26. The system of claim 25 wherein said first and second boxes are fabricated of plastic coated with a metallic layer, the respective layers of each box in electrical contact with each other.

27. The system of claim 26 further comprising a shielded ground conductor for electrically grounding said metallic layers, such that any electromagnetic interference generated within said shield enclosure is intercepted and routed to electrical ground, thereby preventing said interference from affecting the quality of MRI images of the patient.

28. The system of claim 27 further comprising a non-magnetic audio generator responsive to electrical audio-defining signals for generating audio signals, said audio generator disposed within said shield enclosure.

29. The system of claim 28 wherein said audio generator comprises a non-magnetic transducer.

30. The system of claim 28 wherein said audio generator comprises a non-magnetic tube for transmitting said audio signals to a headset.

31. An image generating system for display of images to a patient within the magnetic field of a scanner tunnel of a magnetic resonance imaging scanner, comprising:

a first non-magnetic image generator disposed within said scanner tunnel for generating a visible image in response to first electronic image-defining signals, said first image generator comprising a first electronic liquid crystal display (LCD) panel responsive to said first image-defining signals;

a non-magnetic, non-ferrous shield enclosure for housing said first non-magnetic image generator within said scanner tunnel and within a magnetic field generated within said scanner tunnel during imaging operation of said imaging scanner, said shield enclosure adapted to shield said image generator from RF pulses generated by said imaging scanner during imaging operation such that said RF pulses do not appreciably affect operation of said first image generator, said shield enclosure further adapted to shield said imaging scanner from any electromagnetic interference generated by said first image generator such that said first image generator does not appreciably affect operation of said imaging scanner;

first optical apparatus connected to said shield enclosure for directing said visible image from a penetration in said shield enclosure to a person's eye for viewing by said patient disposed within said scanner tunnel; and an LCD driver circuit mounted on a circuit board and located outside said scanner tunnel and connected to said first image generator via an RF-shielded cable to provide said first electronic image-defining signals.

32. The system of claim 31 wherein said shield enclosure is adapted to perform the function of a Faraday cage.

33. An image generating system for use within a magnetic field of a scanner tunnel of a magnetic resonance imaging scanner, comprising:

a first non-magnetic image generator disposed within said scanner tunnel for generating a visible image in response to first electronic image-defining signals, said first image generator comprising a first electronic display device responsive to said first image-defining signals;

a non-magnetic, non-ferrous shield enclosure for housing said first non-magnetic image generator within said scanner tunnel and within a magnetic field generated within said scanner tunnel during imaging operation of said imaging scanner, said shield enclosure sure for shielding said image generator from RF pulses generated by said imaging scanner during imaging operation such that said RF pulses do not appreciably affect operation of said first image generator, and for shielding said imaging scanner from any electro-magnetic interference generated by said first image generator such that said first image generator does not appreciably affect operation of said imaging scanner, said shield enclosure comprising first and second non-magnetic sliding boxes comprising electrically conductive surfaces, said first box adapted for movement into and out of said second box; and first optical apparatus for directing said visible image for viewing by a person disposed within said scanner tunnel.

34. An image generating system for use within a magnetic field of a scanner tunnel of a magnetic resonance imaging scanner, comprising:

a first non-magnetic image generator disposed within said scanner tunnel for generating a first visible image in response to first electronic image-defining signals, said first image generator comprising a first electronic display device responsive to said first image-defining signals;

a second non-magnetic image generator disposed within said scanner tunnel for generating a second visible image in response to second electronic image-defining signals, said second image generator comprising a second electronic display device responsive to said second image-defining signals;

a non-magnetic, non-ferrous shield enclosure for housing said first and second non-magnetic image generators within said scanner tunnel and within a strong magnetic field generated within said scanner tunnel during imaging operation of said imaging scanner, said shield enclosure adapted to shield said image generators from RF pulses generated by said imaging scanner during imaging operation such that said RF pulses do not appreciably affect operation of said image generators, said shield enclosure further adapted to shield said imaging scanner from any electromagnetic interference generated by said image generators such that said image generators do not appreciably affect operation of said imaging scanner;

first optical apparatus connected to said shield apparatus for directing said first visible image for viewing by a person disposed within said scanner tunnel;

second optical apparatus connected to said shield apparatus for directing said second visible image for viewing by said person; and wherein said first image generator and said first optical apparatus cooperate to direct said first image for viewing by the right eye of said person, and said second image generator and said second optical apparatus cooperate to direct said second image for viewing by the left eye of said person.

35. The system of claim 34 further including apparatus for generating said first and second electronic image-defining signals, said apparatus located outside said scanner tunnel, wherein said first and second electronic image-defining signals are different from each other so as to produce first and second images which are different from each other.

36. The system of claim 35 wherein said generating apparatus is adapted to generate first and second electronic image-generating signals to produce stereoscopic images at the viewer's eyes.

37. The system of claim 34 further comprising a shielded ground conductor for electrically grounding said metallic layers, such that any electromagnetic interference generated within said shield enclosure is intercepted and routed to electrical ground, thereby preventing said interference from affecting the quality of MRI images of the patient.

38. The system of claim 34 further comprising a non-magnetic audio generator responsive to electrical audio-defining signals for generating audio signals, said audio generator disposed within said shield enclosure.

39. The system of claim 38 wherein said audio generator comprises a non-magnetic transducer.

* * * * *